US012654169B2

(12) United States Patent
Blain Christen et al.

(10) Patent No.: US 12,654,169 B2
(45) Date of Patent: Jun. 16, 2026

(54) POINT OF NEED FLUID TRANSPORT DEVICE

(71) Applicant: ARIZONA BOARD OF REGENTS ON BEHALF OF ARIZONA STATE UNIVERSITY, Scottsdale, AZ (US)

(72) Inventors: Jennifer Blain Christen, Chandler, AZ (US); Clifford L Anderson, Tempe, AZ (US); Vi Thanh Nguyen, Phoenix, AZ (US); Michael T. Hansen, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 896 days.

(21) Appl. No.: 17/961,986

(22) Filed: Oct. 7, 2022

(65) Prior Publication Data

US 2023/0109977 A1     Apr. 13, 2023

Related U.S. Application Data

(60) Provisional application No. 63/253,829, filed on Oct. 8, 2021.

(51) Int. Cl.
| | |
|---|---|
| *B01L 3/00* | (2006.01) |
| *A61B 10/00* | (2006.01) |
| *B01L 9/00* | (2006.01) |
| *C12Q 1/6851* | (2018.01) |
| *G01N 35/10* | (2006.01) |

(52) U.S. Cl.
CPC ...... *B01L 3/502715* (2013.01); *C12Q 1/6851* (2013.01); *B01L 2200/04* (2013.01); *B01L 2200/16* (2013.01); *B01L 2300/044* (2013.01);

*B01L 2300/048* (2013.01); *B01L 2300/0636* (2013.01); *B01L 2300/0672* (2013.01); *B01L 2300/1805* (2013.01)

(58) Field of Classification Search
None
See application file for complete search history.

(56) References Cited

U.S. PATENT DOCUMENTS

| | | | | |
|---|---|---|---|---|
| 2009/0117665 | A1* | 5/2009 | Tung ............... | G01N 33/48714 422/68.1 |
| 2012/0183956 | A1* | 7/2012 | Ross ........................ | G01N 1/44 435/306.1 |
| 2013/0115607 | A1* | 5/2013 | Nielsen .................... | C12Q 1/68 435/6.12 |
| 2014/0194305 | A1* | 7/2014 | Kayyem .......... | B01L 3/502784 506/18 |
| 2015/0056716 | A1* | 2/2015 | Oyler ................. | A61B 10/0096 422/550 |
| 2017/0014826 | A1* | 1/2017 | Engel ..................... | B01L 3/523 |

(Continued)

OTHER PUBLICATIONS

Broughton et al., "CRISPR-Cas12-based detection of SARS-COV-2", Nature Biotechnology, vol. 38, Jul. 2020, 870-874.

(Continued)

*Primary Examiner* — Neil N Turk
(74) *Attorney, Agent, or Firm* — Quarles & Brady LLP

(57) ABSTRACT

Provided herein are systems and methods for a point of care apparatus. The point of care apparatus includes a fluid container for receiving a biosample, an intermediate cap, and a cartridge having at least one microfluidic channel.

13 Claims, 5 Drawing Sheets

(56)  References Cited

U.S. PATENT DOCUMENTS

| | | | |
|---|---|---|---|
| 2017/0248622 A1* | 8/2017 | Khattak | G01N 35/0098 |
| 2018/0372595 A1* | 12/2018 | Pais | B01L 3/50273 |
| 2019/0021704 A1* | 1/2019 | Shastry | G01N 33/948 |
| 2020/0191782 A1 | 6/2020 | Katchman et al. | |

OTHER PUBLICATIONS

Fan et al., "Optimization study on the rehydration process of lyophilized human platelets", Chinese Sci Bull, 2011, 56: 455-460, doi: 10.1007/s11434-011-4381-7.

Ghosh et al., "A new microchannel capillary flow assay (MCFA) platform with lyophilized chemiluminescence reagents for a smartphone-based POCT detecting malaria," Microsystems & Nanoengineering (2020)6:5.

Rabe et al., "SARS-COV-2 detection using isothermal amplification and a rapid, inexpensive protocol for sample Inactivation and purification," PNAS, 24450-24458, Sep. 29, 2020, vol. 117, No. 39.

Sherlock Biosciences, Inc, "Instructions For Use, Sherlock, CRISPR SARS-COV-2 kit", LAB-120-0048, rev 07, (2022).

T.U. et al., "A new polymer lab-on-a-chip-(LOC) based on a microfluidic capillary flow assay (MCFA) for detecting unbound cortisol in saliva", Lab Chip, 2020, 20, 1961.

Thermo Scientific "GeneJET Viral DNA and RNA Purification Kit", #K0821, 2021.

* cited by examiner

166

164

200

208

202

204

206

208

206

208

210

POINT OF NEED FLUID TRANSPORT DEVICE

CROSS-REFERENCE TO RELATED APPLICATIONS

This application claims the benefit of U.S. Provisional Application No. 63/253,829 filed Oct. 8, 2021, which is incorporated by reference herein in its entirety.

STATEMENT REGARDING FEDERALLY SPONSORED RESEARCH

Not applicable.

BACKGROUND

There is a need in the art for a low-cost and easy-to-use method to process a biofluid and perform nucleic acid amplification testing in a point of care device that reduces the likelihood of exposing a user to reagents, and protects the reagents from exposure to excessive temperature.

BRIEF SUMMARY

Disclosed are point of care apparatus and methods of using the same for nucleic acid amplification testing of a biofluid. The apparatus and methods disclosed herein provide a system for processing biofluids and reagents that reduces the likelihood of exposing users to the biofluids and reagents used for nucleic acid amplification. The apparatus and methods disclosed herein also allow for prehydration of lyophilized nucleic acid amplification reagents within the device. Proper hydration of the lysis or RT-LAMP reagents improves lysis of the cells (e.g., viral particle capsids) and nucleic acid amplification. Performing prehydration of lyophilized reagents within the disclosed apparatus speeds up hydration of the reagents, which in turn can improve the RT-LAMP reaction by enhancing mixing. The apparatus disclosed herein provides a closed system that reduces exposure of users to the biofluids and reagents, e.g., by eliminating the step of transferring fluid from one container to another in the open air. The apparatus and methods disclosed herein also provide control of temperature to protect the sensitive reagents from being exposed to excessive temperatures.

In some embodiments, the present disclosure provides a point of care apparatus. The point of care apparatus comprises a fluid container configured to receive a biofluid. The fluid container has an open end, where the open end of the fluid container includes a engageable portion. The point of care apparatus further includes an intermediate cap having a chamber formed between a first and second pierceable seal. The intermediate cap further includes an upwardly extending peripheral wall and a downward extending peripheral wall relative to the chamber, where the upwardly extending peripheral wall includes an engagement feature that is engageable with the engageable portion of the fluid container. The point of care apparatus further includes a cartridge having at least one opening in a top surface that is in fluid communication with at least one microfluidic channel that extends within the cartridge. The cartridge further includes a collar that extends from the top surface and defines a passageway that is in fluid communication with the at least one opening in the cartridge. The collar has an engageable portion, where the downwardly extending peripheral wall of the intermediate cap includes an engagement feature that is engageable with the engageable portion of the collar. The point of care apparatus includes a first piercing insert configured between the first pierceable seal and the open end of the fluid container. The first piercing insert has a piercing feature and an opening extending through the first piercing insert, where engagement between the engagement feature of the upwardly extending peripheral wall of the intermediate cap and the engagement portion of the fluid container bias the piercing feature of the first piercing insert to pierce the first pierceable seal to place the fluid container in fluid communication with the passageway of the intermediate cap. The point of care apparatus further includes a second piercing insert configured between the second pierceable seal and the top surface of the cartridge. The second piercing insert having a piercing feature, where engagement between the engagement feature of the downwardly extending peripheral wall of the intermediate cap and the engageable portion of the collar bias the piercing feature of the second piercing insert to pierce the second pierceable seal to place the at least one microfluidic channel in fluid communication with the passageway of the intermediate cap.

In some embodiments, the present disclosure provides a point of care apparatus. The point of care apparatus includes a fluid container configured to receive a biofluid. The fluid container has an open end, and where the open end of the fluid container includes a engageable portion. The point of care apparatus further includes an intermediate cap having a chamber formed between a first and second pierceable seal. The intermediate cap further includes an upwardly extending peripheral wall and a downward extending peripheral wall relative to the chamber, where the upwardly extending peripheral wall includes an engagement feature that is engageable with the engageable portion of the fluid container. The point of care apparatus includes a first piercing insert configured between the first pierceable seal and the open end of the fluid container. The first piercing insert has a piercing feature and an opening extending through the first piercing insert, where engagement between the engagement feature of the upwardly extending peripheral wall of the intermediate cap and the engageable portion of the fluid container bias the piercing feature of the first piercing insert to pierce the first pierceable seal to place the fluid container in fluid communication with the passageway of the intermediate cap. The chamber in the intermediate cap includes lysis reagents.

In some embodiments, the present disclosure provides a point of care apparatus. The point of care apparatus includes a cartridge having at least one opening in a top surface that is in fluid communication with at least one microfluidic channel that extends within the cartridge. The cartridge further includes a collar that extends from the top surface and defines a passageway that is in fluid communication with the at least one opening in the cartridge. The collar has a engageable portion. The point of care apparatus further includes one or more vents in fluid communication with the at least one microfluidic channel, and wherein the vent includes a gas permeable membrane. The point of care apparatus further includes one or more reagents for performing an amplification reaction to generate amplification products of a target nucleic acid. The point of care apparatus further includes a heater configured to accelerate reaction kinetics of the amplification reaction of the target nucleic acid.

BRIEF DESCRIPTION OF THE DRAWINGS

The accompanying drawings, which are incorporated in and form a part of this specification, illustrate example embodiments of the invention and, together with the description, serve to explain the principles of certain embodiments.

DETAILED DESCRIPTION

Figures 1, 2:
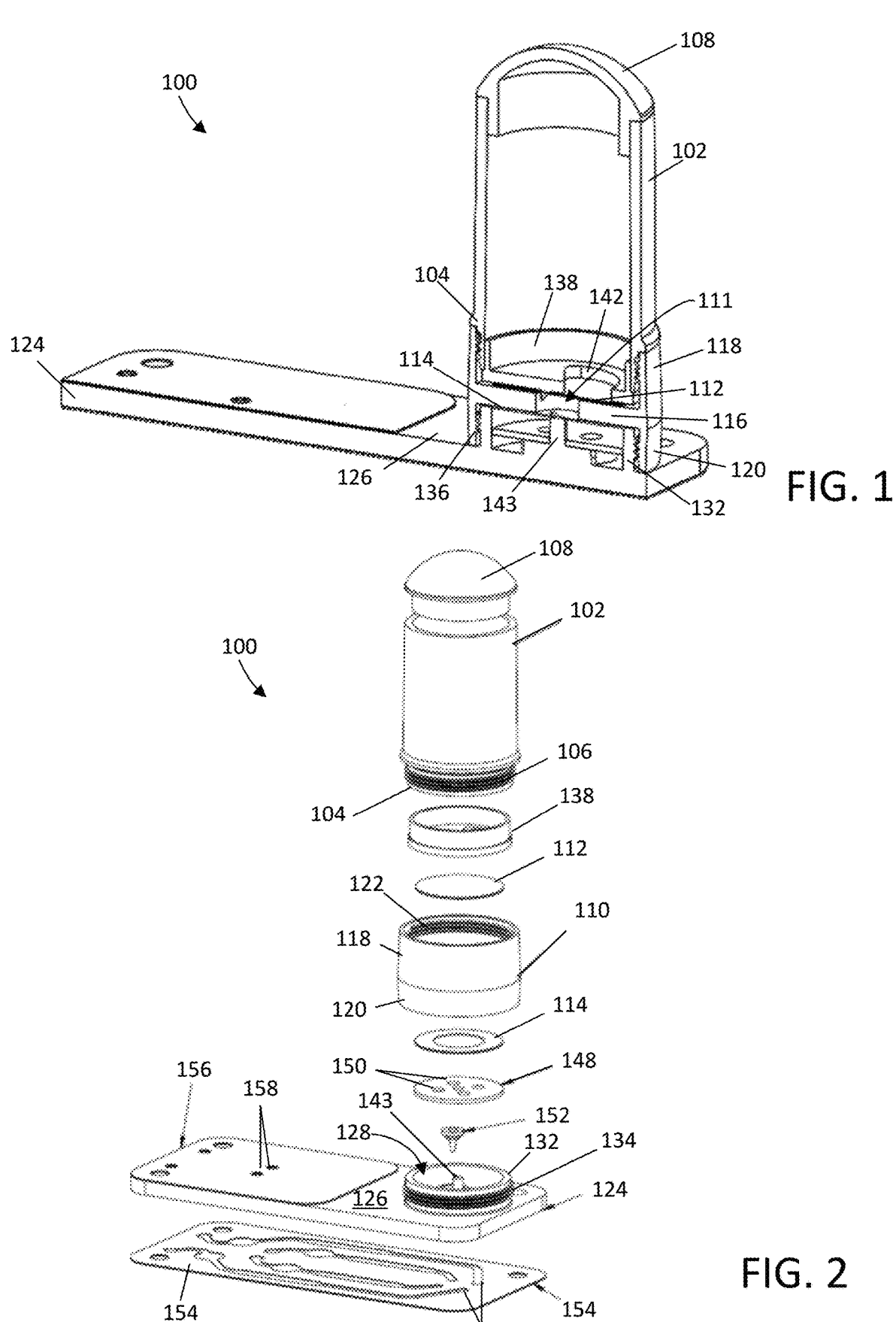
FIG. 1 is a cross-sectional view of a point of care apparatus according to some embodiments of the present disclosure.
FIG. 2 is an exploded view of a point of care apparatus according to some embodiments of the present disclosure.
Figure 3:
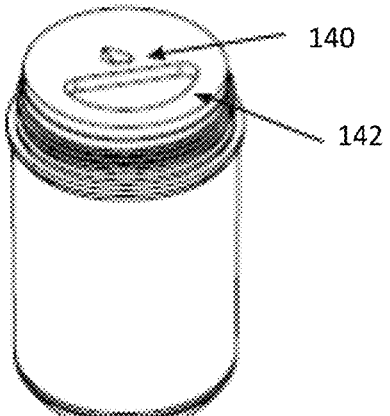
FIG. 3 is a perspective view of a first insert having a first piercing according to some embodiments of the present disclosure.
Figure 4:
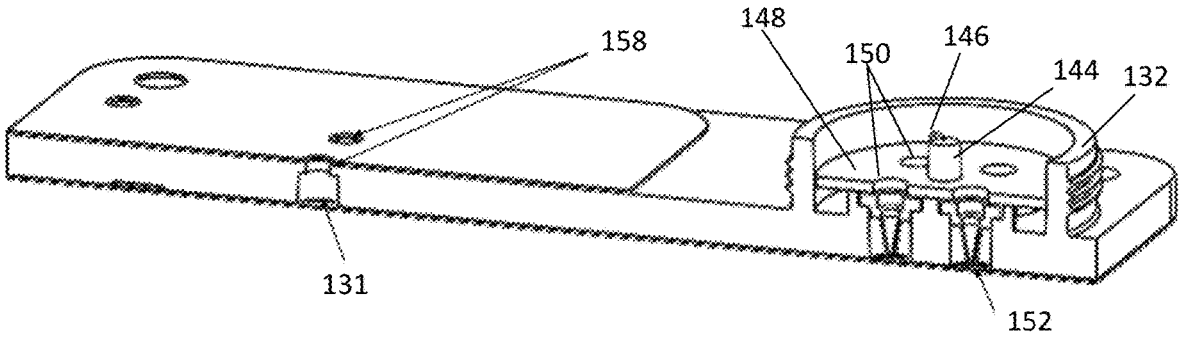
FIG. 4 is a cross-sectional, perspective view of a cartridge, spacer, and valves according to some embodiments of the present disclosure.
Figure 5:
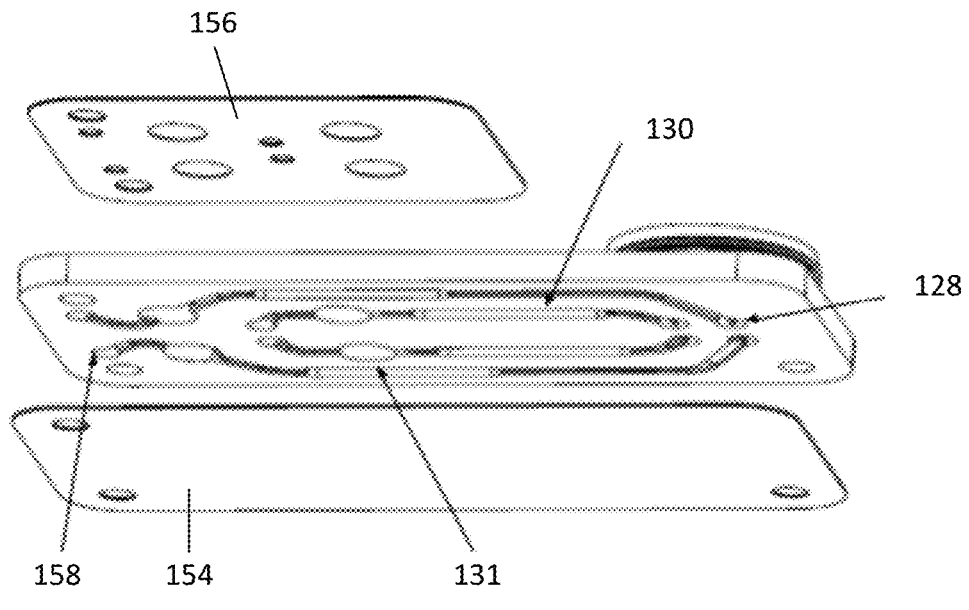
FIG. 5 is an exploded view of the cartridge of FIG. 4.
Figure 6:
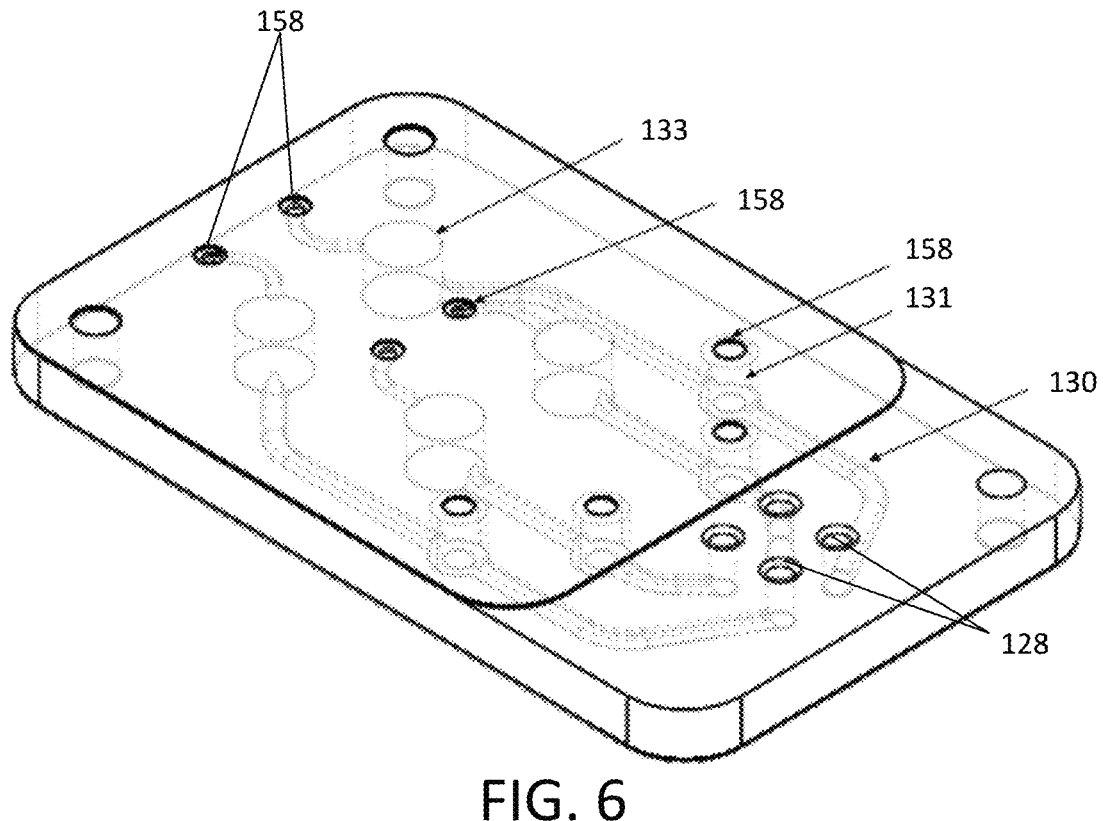
FIG. 6 is a perspective view of a cartridge having micro-fluidic channel and vents according to some embodiments of the present disclosure.

The following discussion is presented to enable a person skilled in the art to make and use embodiments of the invention. Various modifications to the illustrated embodiments will be readily apparent to those skilled in the art after having studied the teachings in this disclosure, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans, after having studied the teachings in this disclosure, will recognize the examples provided herein have many useful alternatives and fall within the scope of embodiments of the invention.

A point of care apparatus and method of using the same for use in clinical and non-clinical settings is described herein. The apparatus is generally useful for nucleic acid amplification testing of a biological fluid ("biofluid") sample, and optional subsequent quantitative detection of the presence or absence of a target nucleic acid using a reader. As used herein, the terms "biological fluid" or "biofluid" relate to any fluid produced from a subject including, without limitation, saliva, blood, serum, urine, cerebrospinal fluid, interstitial fluid, cervical fluid, wound fluid, seminal fluid, and other fluid samples.

As used herein, "subject" or "patient" refers to mammals and non-mammals. A "mammal" may be any member of the class Mammalia including, but not limited to, humans, non-human primates (e.g., chimpanzees, other apes, and monkey species), farm animals (e.g., cattle, horses, sheep, goats, and swine), domestic animals (e.g., rabbits, dogs, and cats), or laboratory animals including rodents (e.g., rats, mice, and guinea pigs). Examples of non-mammals include, but are not limited to, birds, and the like. The term "subject" does not denote a particular age or sex. In one specific embodiment, a subject is a mammal, preferably a human. The subject may have or suffer from, or be suspected of having or suffering from, a disease, condition, or disorder.

In particular embodiments, the provided apparatus and methods can be used to test a biofluid sample that has been allotted appropriate reaction time to amplify one or more target nucleic acids, including target nucleic acids indicative of potential pathogens, or control nucleic acids within the biofluid sample to generate amplification products. An "amplification product" or "amplicon" is a piece of nucleic acid that is the product of amplification or replication events. The amplification product may also be a source of further amplification or replication events. The "amplification" refers to production of one or more copies of nucleic acid sequence. Amplification of the nucleic acid sequence may be accomplished by various amplification methods known in the art including isothermal and non-isothermal amplification methods.

In some embodiments, the subject may have or suffer from, or be suspected of having or suffering from, an infection by a pathogen. "Pathogen" means an organism that can produce disease in a subject. Examples of pathogens include, without limitation, viruses, bacteria, fungi, and parasites.

The target nucleic acid and the control nucleic acid can, but need not, originate from the same source. For example, the target nucleic acid may originate from a pathogen and the control nucleic acid may originate from the subject. In other embodiments, the both the target and control nucleic acids may originate from the subject. In yet other embodiments, both the target and control nucleic acids may originate from a pathogen.

Some nucleic acid amplification processes can take more than 30 minutes or an hour for target nucleic acids in a biofluid to be properly amplified into a detection sample. In some cases, it may be useful for a user to start the amplification process prior to arriving at a sample reader that reads the detection sample.

In some embodiments, the apparatus and methods described herein are capable of analyzing samples at the point of care rather than in a laboratory. As used herein, the term "point of care" or "point of need," which are used interchangeably, can be defined to mean a location on or near a site of patient care where medical or medically related services such as medical testing and/or treatment are provided, including but not limited to hospitals, emergency departments, intensive care units, primary care setting, medical centers, patient homes, physician offices, pharmacies, or sites of an emergency. In some embodiments, "point of care" or "point of need" can be defined as an entry point to a variety of workplaces or gathering locations, such as, for example, airports, train stations, nursing homes, schools, etc. Allowing for the testing of samples collected at or brought to the entry point aids in restricting access to the workplace or gathering location for those who test positive. Further, in some embodiments, the systems and devices of this disclosure are capable of analyzing samples at home to provide regular checks of individuals in a multi-family environment, such as assisted living facilities, dormitories, etc.

FIGS. 1-6 illustrate a point of care apparatus 100 according to some embodiments of the present disclosure. The point of care apparatus 100 includes a fluid container 102 configured to receive a biofluid. The fluid container 102 has an open end 104, where the open end 104 includes an engageable portion 106 (e.g., threaded portion, twist-and-lock, snap fit). In some embodiments, a closed end of the fluid container 102 may include a diaphragm pump 108 configured to dispense biofluids from the fluid container 102.

In some embodiments, the point of care apparatus 100 further includes an intermediate cap 110. The intermediate cap includes a chamber 111 formed between a first and second pierceable seal 112, 114. In some embodiments, the intermediate cap 110 includes a base wall 116 having a top surface that is configured to receive the first pierceable seal 112, and a bottom surface that is configured to receive the second pierceable seal 114. The chamber 111 forms a passageway through the base wall 116. The intermediate cap 110 includes an upwardly extending peripheral wall 118, and a downwardly extending peripheral wall 120 relative to the chamber 111. In some embodiments, the upwardly extending peripheral wall 118 includes an engagement feature 122 (e.g., threads, twist-and-lock features, snap fit features) that is engageable with the engageable portion 106 of the fluid container 102.

In some embodiments, the point of care apparatus 100 includes a cartridge 124. The cartridge 124 includes a top surface 126 having at least one opening 128 that is in fluid communication with at least one microfluidic channel 130 within the cartridge 124. The cartridge 124 includes a collar 132 that extends from the top surface 126 and defines a passageway that is in fluid communication with the at least one opening 128 in the cartridge 124. The collar 132 includes an engageable portion 134 (e.g., threaded portion, twist-and-lock, snap fit) that is engageable with an engagement feature 136 (e.g., threads, twist-and-lock features, snap fit features) of the downwardly extending peripheral wall 120.

In some embodiments, the point of care apparatus 100 includes a first piercing insert 138 configured between the first pierceable seal 112 and the open end 104 of the fluid container 102. The first piercing insert 138 includes a piercing feature 140 and an opening 142 extending through the piercing insert 138. In some embodiments, engagement between the engagement feature 122 of the upwardly extending peripheral wall 118 and the engagement portion 106 of the fluid container 102 bias (e.g., via rotation of the fluid container 102) the piercing feature 140 to pierce the first pierceable seal 112 to place the fluid container 102 in fluid communication with the chamber 111 of the intermediate cap 110.

In some embodiments, the point of care apparatus 100 includes a second piercing insert 144 having a piercing feature 146 configured between the second pierceable seal 114 and the top surface 126 of the cartridge 124. In some embodiments, engagement between engagement feature 136 of the downwardly extending peripheral wall 120 of the intermediate cap 110 and the engageable portion 134 of the collar 132 bias the piercing feature of the second piercing insert 143 to pierce the second pierceable seal 114 to place the at least one microfluidic channel 130 in fluid communication with the chamber 111 of the intermediate cap 110.

In some embodiments, the second piercing insert 143 is part of the cartridge 124, i.e., a projection from the top surface 126 of the cartridge 124. Alternatively or additionally, the second piercing insert 143 may be a separate part from the cartridge 124 that is coupled, or directly attached, to the cartridge 124.

In some embodiments, the point of care apparatus 100 includes a spacer 148 positioned in the collar 132. The spacer 148 includes at least one opening 150 with a valve 152 to reduce backflow of fluid to the at least one microfluidic channel 130. In some embodiments, the valve 152 is a duckbill valve. In some embodiments, there is one opening 150. In some embodiments, there may be at least 1 to less than 10 openings 150. For example, there may be at least 1 opening, at least 2 openings, at least 3 openings, at least 4 openings, at least 5 openings, less than 6 openings, less than 7 openings, less than 8 openings, less than 9 openings, or less than 10 openings.

In some embodiments, the point of care apparatus 100 includes a heater (not shown). The heater may be external to the apparatus 100, and configured to apply heat to any part of the apparatus 100, but particularly at least one or more of the fluid container 102, the intermediate cap 110, the cartridge 124, or combinations thereof. In some embodiments, the heater is configured adjacent or in contact with at least one of the microfluidic channel 130.

In some embodiments, the cartridge 124 includes a bottom chip 154 and a top chip 156 that enclose the at least one microfluidic channel 130. In some embodiments, the top chip 156 includes one or more vent 158 in fluid communication with the at least one microfluidic channel 130. In some embodiments, the one or more vents 158 include a gas permeable membrane. The gas permeable membrane allows for gases (e.g., moisture) to vent from the at least microfluidic channel 130 during heating, but reduces the likelihood of, or entirely prevents, the biofluid and/or reagents from exiting the apparatus 100 through the vents 158.

In some embodiments, the chamber 111 in the intermediate cap 110 includes lysis reagents. Lysis reagents may be used for breaking open cells and analyzing labile macromolecules within the cells (e.g., DNA). The lysis reagents may be in the form lyophilized pellets or in a solution. Suitable lysis reagents include, without limitation, proteases (e.g., proteinase K), buffered salts (e.g., Tris-HCl), ionic salts, (e.g., NaCl), surfactants, chaotropic salts, chelating agents such as EDTA, cofactors, carrier RNA, or combinations thereof.

In some embodiments, the chamber 111 of the intermediate cap 110 and/or the at least one microfluidic channel 130 includes one or more reagents for performing an amplification technique therein. The reagents may be placed in pockets 131 within the microfluidic channel 130. In some embodiments, the at least one microfluidic channel 130 further includes an analysis window 133. The biofluid flowing through the at least one microfluidic channel 130 may transport the reagents from the pockets 131 to the analysis window 133 (e.g., by dissolving or otherwise entraining the reagents therein).

Suitably, the amplification technique is an isothermal amplification technique that may additionally comprise reverse transcription (RT) for detection of RNA species. In some cases, the isothermal amplification technique is loop-mediated isothermal amplification (LAMP). Other isothermal amplification techniques may alternatively be used, and include, without limitation, strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), single primer isothermal amplification (SPIA), recombinase polymerase amplification (RPA), polymerase spiral reaction (PSR), and reverse transcription polymerase chain reaction (RT-PCR). In some cases, reagents for isothermal amplification will vary based on the isothermal amplification technique employed and generally comprise primers and a strand-displacing DNA polymerase, a reverse transcriptase (for detection of RNA species), and/or a DNA helicase. In some cases, the reagents further comprise synthetic nucleic acids (e.g., riboregulators) configured to detect natural nucleic acids from one or more pathogens such as viruses, bacteria, fungi, and parasites.

Figure 7:
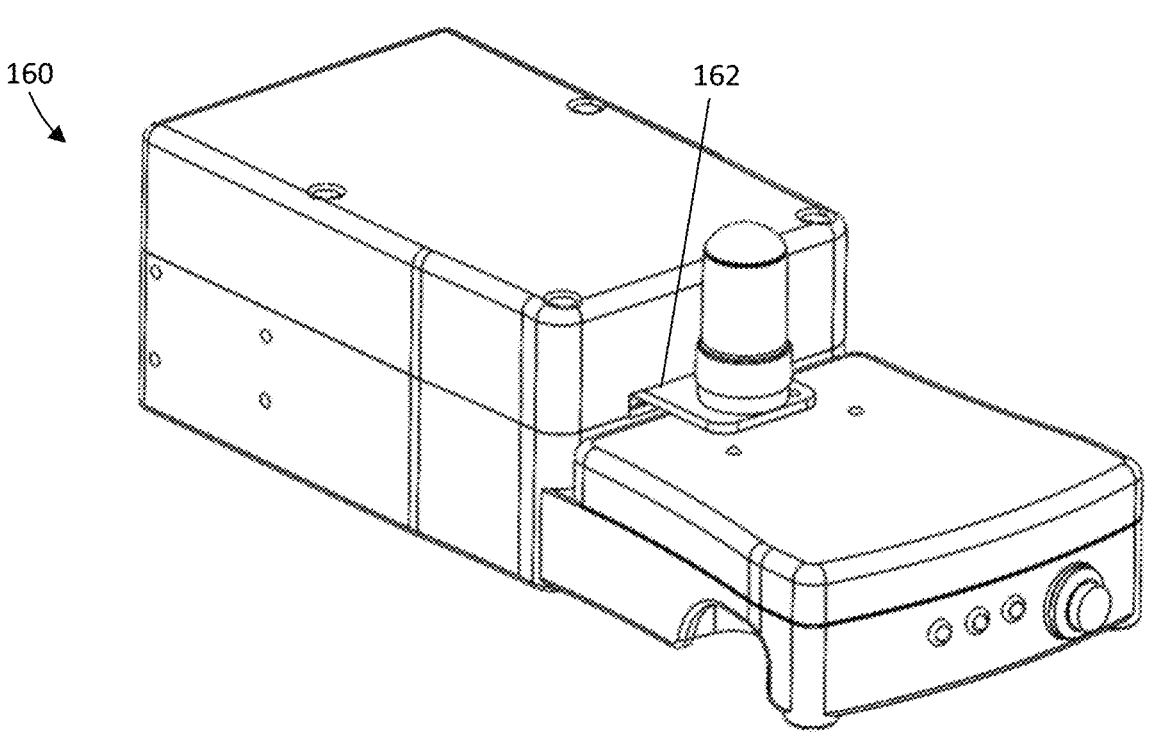
FIG. 7 is a perspective view of a point of care apparatus according to some embodiments of the present disclosure.
Figure 8:
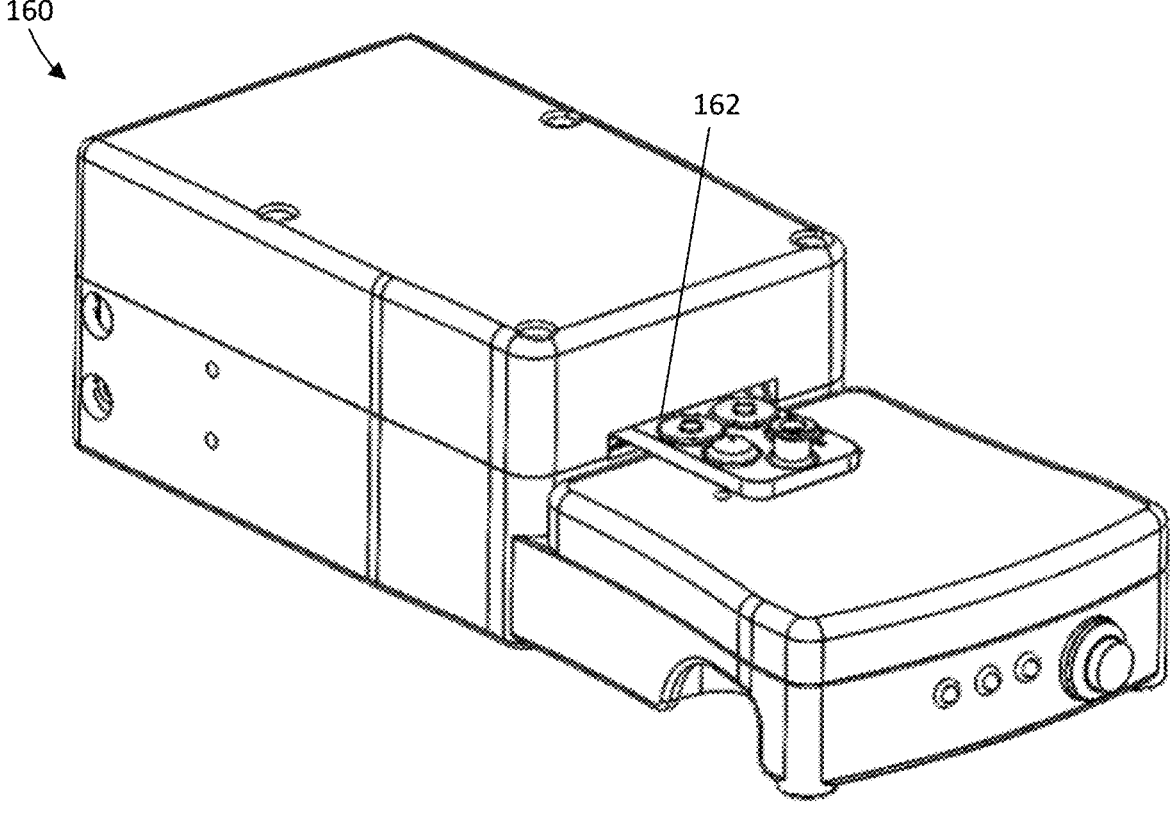
FIG. 8 is a perspective view of the point of care system having a reader according to some embodiments of the present disclosure.

In some embodiments, the present disclosure provides a reader 160 that is configured to accept (or receive) the cartridge 124 of the point of care apparatus 100 and produce a qualitative or quantitative output, as shown in FIGS. 7-8. The reader 160 includes a detection inlet 162 that receives the cartridge 124. The reader may provide electromagnetic radiation that may be absorbed by the biofluid sample within the cartridge 124. The electromagnetic radiation may be of any suitable wavelength that can provide a detectable signal indicating the presence or absence of an amplification product of a target nucleic acid. In some embodiments, the electromagnetic radiation may be of any suitable wavelength that can provide a detectable signal indicating the presence or absence of an amplification product of a control nucleic acid. In some embodiments, the excitation array provides electromagnetic radiation in the infrared, visible, or ultraviolet spectrums. The reader 160 may emit broadband or narrowband electromagnetic spectrums.

The reader 160 may include a photodetector that detects any suitable wavelength of electromagnetic radiation. In some embodiments, the photodetector detects electromagnetic radiation in the infrared, visible, or ultraviolet spectrums. The photodetector may include an array connected to a readout circuit, which can include a microchip. The photodetector can wirelessly communicate or communicate through a wired connection to a processor (not shown) that can decode and translate intensities sent via a digital signal that originate from a current signal. The detection sample may include biomarkers, chromophores, fluorophores, dyes, and other compounds or substances capable of emitting light of a second wavelength or color when stimulated by a first light of a first wavelength or color. The presence of amplification products of the target and/or control nucleic acid sequence in the second biofluid sample may alter electromagnetic radiation intensity emitted at the second wavelength relative to an amplification product free second biofluid sample. The photodetector can detect the light of the second color and output the current which is then transmitted to the processor. The intensity of the detected light allows for determination of the presence or absence of the target nucleic acid and/or control nucleic acid target. The processor can output qualitative or quantitative results that can be used for epidemiological data collection and studies.

In some embodiments, the reader 160 can further include an indicator (not shown). The indicator can include one or more of an audio, visual, or tactile indication. For example, the indicator may output a light (e.g., a green light or a red light) if a specific pathogen at a predetermined level is found (or not found) in the detection sample.

Figure 9:
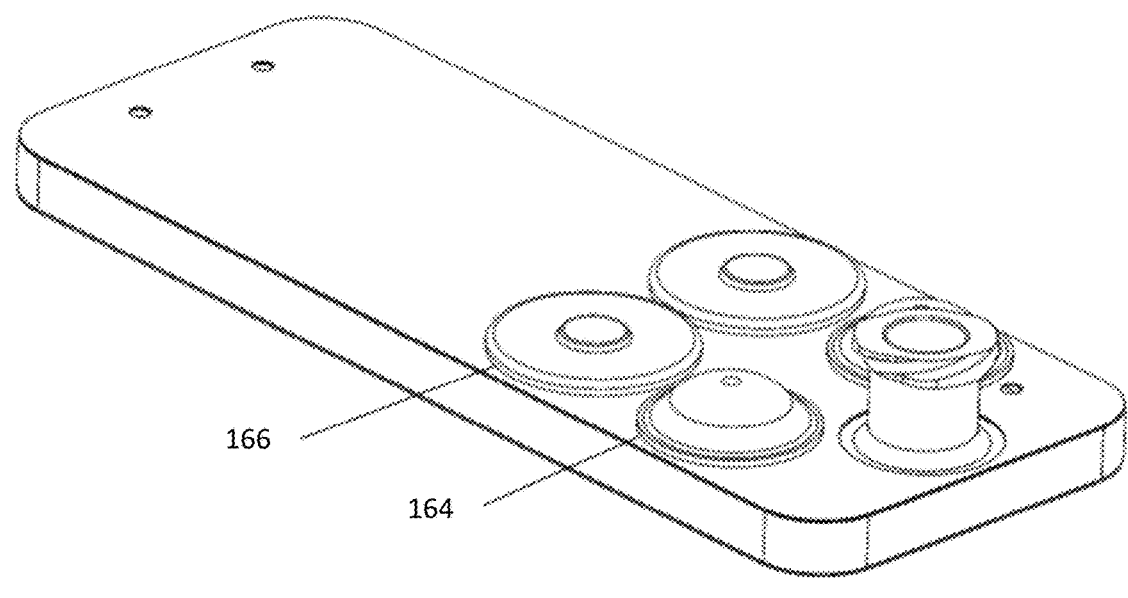
FIG. 9 is a perspective view of a cartridge with blisters in accordance with some embodiments of the present disclosure.

As shown in FIGS. 8-9, in some embodiments, the cartridge 124 includes blisters 164 and valves 166. The blisters 164 may supply reagents and fluids to the cartridge 124 on demand (e.g., via actuation that pierces the blister). Methods:

The present disclosure provides a method of using the point of care apparatus 100. In some embodiments, the method includes collecting a biofluid in the fluid container 102, e.g., by obtaining a saliva sample from subject. The method further includes engaging the engageable portion 106 of the fluid container 102 with the engagement feature 122 of the upwardly extending peripheral wall 118 to bias the piercing feature 140 of the first piercing insert 138 to pierce the first pierceable seal 112 to place the biofluid sample in the fluid container 102 in fluid communication with the lysate reagents within the chamber 111 of the intermediate cap 110.

In some embodiments, the method includes mixing the biofluid sample with the lysis reagents for a duration. Mixing the reagents may include inverting the fluid container 102 and the intermediate cap 110 for a number of times, e.g., at least 2 times to 20 times, or more. In some embodiments, the biofluid is heated prior to mixing the reagents, where moisture produced from heating the biofluid may contact and pre-hydrate lysis reagents within the intermediate cap 110. In some embodiments, the method further includes engaging the engageable portion 134 of the collar 132 with engagement feature 136 of the downwardly extending peripheral wall 120 to bias the piercing feature of the second piercing insert 143 to pierce the second pierceable seal 114 to place the biofluid sample in fluid communication with the at least one microfluidic channel 130 in the cartridge 124.

Rapid inactivation of SARS-CoV-2 or other virions and endogenous nucleases in a saliva sample followed by reverse-transcription loop-mediated isothermal amplification (RT-LAMP) has achieved a sensitivity of 50 viral RNA copies per microliter of sample. Saliva processing for in vitro diagnostic tests often involves the use of lysis reagents, such as proteinase K, to lyse viral particle capsids. This can be done at room temperature but elevated temperature of 55° C., for example, enhances this process. After the lysate reaction is complete, the saliva is then heated to 95° C. to denature the lysate, to disrupt viral genomes, and to lower the viscosity of the saliva. In some embodiments, the method includes heating the biofluid sample within the fluid container 102. In some embodiments, heating occurs at a lysis temperature of about 50° C. to 65° C. (e.g., proteinase K sample digestion) for a duration (e.g., from about 1 minute to about 15 minutes), followed by an inactivation temperature at about 90° C. to about 100° C. (e.g., proteinase K inactivation) for a duration (e.g., about 1 minute to about 10 minutes).

In some embodiments, the apparatus is then placed, while maintaining inversion to keep the sample in the fluid container, into a heater. The heater may provide two heating periods as described above. During the second heating step, venting of a moisture product may occur through the intermediate cap into the inverted cartridge microfluidic channel and into the lyophilized regions to prehydrate the reagents. However, a single heating period of 95° C. may be used depending on the assay protocol. A cooling period follows to allow safe handling and introduction of the processed sample into the microfluidic cartridge.

For the heating process in the fluid container, the heating zone may encompass the circumference of the fluid container from the bottom up to and including the intermediate cap containing residual sample-reagent mixture, to ensure all of the sample mixed with reagent reaches the target temperature.

In some embodiments, the method includes contacting the biofluid sample in the at least one microfluidic channel with one or more reagents for performing an amplification reaction to generate amplification products of a target nucleic acid. LAMP reagents, for example, are degraded at elevated temperatures. While the LAMP reaction preferably occurs in the range of 61 to 65° C., the temperature of 95° C. commonly used in saliva sample processing would render the proximate LAMP reagents and/or dyes ineffective in a point of care device.

The thermal insulating properties of the remainder of the intermediate cap and the cartridge, considering the material properties and geometry, allows for a temperature drop relative to the heating zone during the heating step, thus maintaining the temperature of lyophilized reagents in the cartridge below about 65° C. An additional embodiment may use a lid to make contact with the now top side of the inverted cartridge whereby the lid serves as a heat sink to moderate the temperature of the cartridge and reagents contained therein. Temperature moderation of the cartridge helps reduce LAMP reagent thermal degradation and also enhances condensation in the lyophilized region for improved pre-hydration.

The lyophilized LAMP or other amplification reagents may be specific to each of the individual microfluidic channel. The amplification reagent can be lyophilized directly into a lyophilization trough, or it can be pelletized and placed into a pocket which may have a cylindrical, semi-spherical or other shape, or into each analysis well. There can be one or multiple pellets per channel, in one or more pockets per channel. In each of these various cases, pre-hydration from heating saliva, or any other fluid, such as biofluids, may be beneficial to the process.

In some embodiments, the method further includes inserting the cartridge 124 into a reader 160 to detect the presence or absence of a target nucleic acid.

Figure 10:
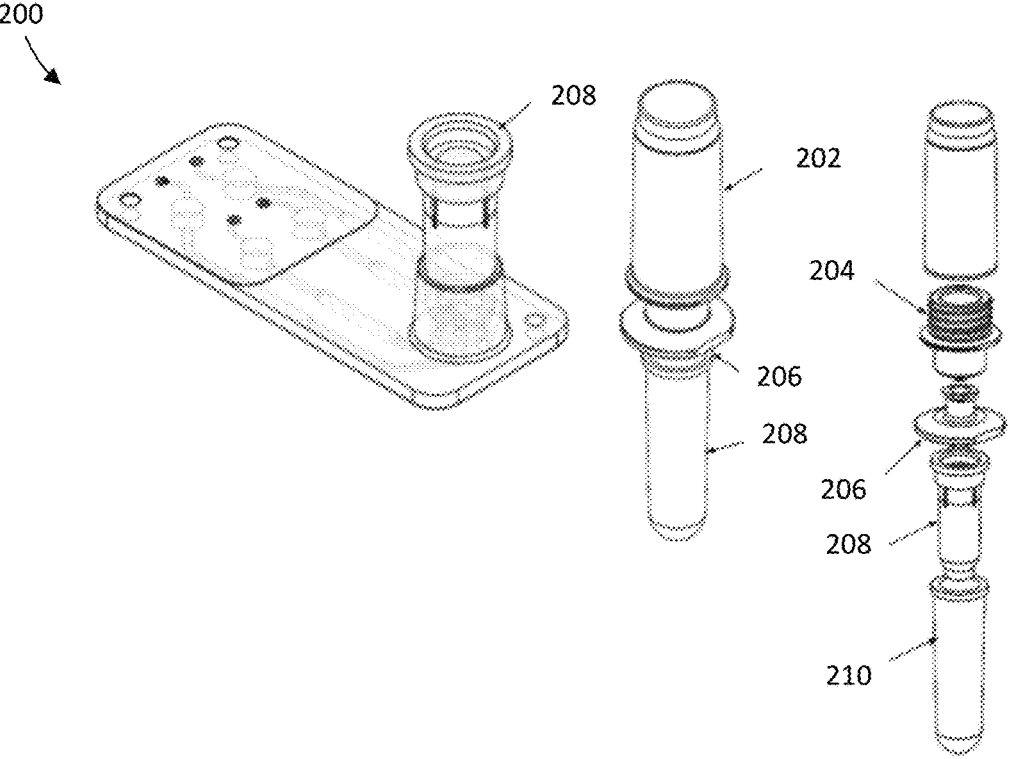
FIG. 10 is an exploded view of a cartridge according to some embodiments of the present disclosure.

As shown in FIG. 10, in some embodiments, the point of care apparatus 200 includes a fluid container 202, a threaded adaptor 204 that threadingly engages the fluid container 202, a twist adapter assembly 206, 208 coupled to the threaded adaptor 204, a silica column 210 coupled to the twist adaptor assembly 208. A biofluid may be collected in the fluid container 202, and portions of the biofluid may be trapped on the silica column 210. In use, a user may detach adaptor 204, attach a syringe, and pump lysis reagents through the silica column 210. A wash solution may then be passed through the silica column 210. A waste column may collect the wash solution. The silica column 210 may be attached to cartridge 124. A buffered solution may then be passed over the silica column to elute the biofluid in the silica column 210 into the at least one microfluidic channel 130 of the cartridge 124. The reader 160 may automatically detect the presence or absence of a target nucleic acid using the methods described above.

EXEMPLARY EMBODIMENTS

1. A point of care apparatus comprising:
a fluid container configured to receive a biofluid, the fluid container having an open end, and wherein the open end of the fluid container includes an engageable portion;
an intermediate cap having a chamber formed between a first and second pierceable seal, the intermediate cap having an upwardly extending peripheral wall and a downwardly extending peripheral wall relative to the chamber, wherein the upwardly extending peripheral wall includes an engagement feature that couples the intermediate cap to the fluid container;
a cartridge having at least one opening in a top surface that is in fluid communication with at least one microfluidic channel that extends within the cartridge, the cartridge having a collar that extends from the top surface and defines a passageway that is in fluid communication with the at least one opening in the cartridge, the collar having an engageable portion, wherein the downwardly extending peripheral wall of the intermediate cap includes an engagement feature that couples the cartridge with the engageable portion of the collar;
a first piercing insert configured between the first pierceable seal and the open end of the fluid container, the first piercing insert having a piercing feature and an opening extending through the first piercing insert, wherein engagement between the engagement feature of the upwardly extending peripheral wall of the intermediate cap and the engageable portion of the fluid container bias the piercing feature of the first piercing insert to pierce the first pierceable seal to place the fluid container in fluid communication with the chamber of the intermediate cap; and
a second piercing insert configured between the second pierceable seal and the top surface of the cartridge, the second piercing insert having a piercing feature, wherein engagement between engagement feature of the downwardly extending peripheral wall of the intermediate cap and the engageable portion of the collar bias the piercing feature of the second piercing insert to pierce the second pierceable seal to place the at least one microfluidic channel in fluid communication with the chamber of the intermediate cap.

2. The point of care apparatus of embodiment 1, wherein the engageable portion of the open end of the fluid contain includes a threaded portion,
wherein the engagement feature of the upwardly peripheral wall includes threads, wherein the threads are engageable with the threaded portion of the fluid container to reversibly couple the intermediate cap to the fluid container,
wherein the engageable portion of the collar includes a threaded portion, and
wherein engagement feature of the downwardly extending peripheral wall includes threads that are engageable with the threaded portion to reversibly couple the cartridge with the threaded portion of the collar.

3. The point of care apparatus of embodiment 1, wherein the chamber in the intermediate cap includes lysis reagents.

4. The point of care apparatus of embodiment 3, wherein the lysis reagents comprise proteinase K.

5. The point of care apparatus of embodiment 3, wherein the lysis reagents are in the form of lyophilized pellets.

6. The point of care apparatus of embodiment 1, wherein the second piercing insert is directly coupled to the top surface of the cartridge.

7. The point of care apparatus of embodiment 1 further comprising a spacer positioned in the collar, the spacer having at least one opening with a valve to reduce backflow of fluid to the at least one microfluidic channel.

8. The point of care apparatus of embodiment 7, wherein the valve is a duckbill valve.

9. The point of care apparatus of embodiment 1, wherein the chamber in the intermediate cap includes one or more reagents for performing an amplification reaction to generate amplification products of a target nucleic acid.

10. The point of care apparatus of embodiment 1, wherein the at least one microfluidic channel includes one or more reagents for performing an amplification reaction to generate amplification products of a target nucleic acid.

11. The point of care apparatus of embodiment 1 further comprising at least one heater.

12. The point of care apparatus of embodiment 11, wherein the at least one heater is configured to heat the fluid container, the intermediate cap, the at least one microfluidic channel, or combinations thereof.

13. The point of care apparatus of embodiment 11, wherein the heater is configured to accelerate reaction kinetics of an amplification reaction of a target nucleic acid.

14. The point of care apparatus of embodiment 1, wherein the cartridge includes one or more vents in fluid communication with the at least one microfluidic channel, and wherein the vent includes a gas permeable membrane.

15. The point of care apparatus of embodiment 1, wherein a closed end of the fluid container includes a diaphragm pump configured to dispense biofluids from the fluid container.

16. A point of care apparatus comprising:

a fluid container configured to receive a biofluid, the fluid container having an open end, and wherein the open end of the fluid container includes an engageable portion;

an intermediate cap having a chamber formed between a first and second pierceable seal, the intermediate cap having an upwardly extending peripheral wall and a downwardly extending peripheral wall relative to the chamber, wherein the upwardly extending peripheral wall includes an engagement feature that reversibly couples the intermediate cap to the fluid container;

a first piercing insert configured between the first pierceable seal and the open end of the fluid container, the first piercing insert having a piercing feature and an opening extending through the first piercing insert, wherein engagement between the engagement feature of the upwardly extending peripheral wall of the intermediate cap and the engageable portion of the fluid container bias the piercing feature of the first piercing insert to pierce the first pierceable seal to place the fluid container in fluid communication with the chamber of the intermediate cap; and wherein the chamber in the intermediate cap includes lysis reagents.

17. The point of care apparatus of embodiment 16, wherein the engageable portion of the open end of the fluid contain includes a threaded portion, and wherein the engagement feature of the upwardly peripheral wall includes threads, wherein the threads are engageable with the threaded portion of the fluid container to reversibly couple the intermediate cap to the fluid container.

18. The point of care apparatus of embodiment 16, wherein the lysis reagents comprise proteinase K.

19. The point of care apparatus of embodiment 16, wherein the lysis reagents are in the form of lyophilized pellets.

20. The point of care apparatus of embodiment 16, wherein the chamber in the intermediate cap includes one or more reagents for performing an amplification reaction to generate amplification products of a target nucleic acid.

21. A point of care apparatus comprising:

a cartridge having at least one opening in a top surface that is in fluid communication with at least one microfluidic channel that extends within the cartridge, the cartridge having a collar that extends from the top surface and defines a passageway that is in fluid communication with the at least one opening in the cartridge, the collar having an engageable portion;

one or more vents in fluid communication with the at least one microfluidic channel, and wherein the vent includes a gas permeable membrane;

one or more reagents for performing an amplification reaction to generate amplification products of a target nucleic acid; and a heater configured to accelerate reaction kinetics of the amplification reaction of the target nucleic acid.

22. A method of using the point of care device of embodiment 3, the method comprising:

engaging the engageable portion of the fluid container, the fluid container having a biofluid sample therein, with the engagement feature of the upwardly extending peripheral wall to bias the piercing feature of the first piercing insert to pierce the first pierceable seal to place the biofluid sample in the fluid container in fluid communication with the lysis reagents within the chamber of the intermediate cap; and mixing the biofluid sample with the lysis reagents for a duration.

23. The method of embodiment 22, wherein mixing the biofluid sample includes inverting the fluid container and the intermediate cap.

24. The method of embodiment 22 further comprising:

engaging the engageable portion of the collar with the engagement feature of the downwardly extending peripheral wall to bias the piercing feature of the second piercing insert to pierce the second pierceable seal to place the biofluid sample mixed with the lysis reagents in fluid communication with the at least one microfluidic channel in the cartridge.

25. The method of embodiment 24 further comprising:

contacting the biofluid sample in the at least one microfluidic channel with one or more reagents for performing an amplification reaction to generate amplification products of a target nucleic acid.

26. The method of embodiment 22 further comprising:

heating the biofluid sample within the fluid container, wherein heating the biofluid sample produces a moisture product, and wherein the moisture product hydrates one or more lyophilized reagents within the intermediate cap or cartridge.

27. The method of embodiment 22 further comprising:

heating the biofluid in the fluid container to a lysis temperature.

28. The method of embodiment 27, wherein the lysis temperature ranges between 50° C. to 65° C.

29. The method of embodiment 27 further comprising:

heating the biofluid sample within the fluid container to an inactivation temperature.

30. The method of embodiment 27, wherein the inactivation temperature ranges between 90° C. to 100° C.

The previous description, including disclosed embodiments, is provided to enable any person skilled in the art to make or use the invention. Various modifications to these embodiments will be readily apparent to those skilled in the art, and the generic principles defined herein may be applied to other embodiments without departing from the spirit or scope of the invention. Thus, the invention is not intended to be limited to the embodiments shown herein but is to be accorded the widest scope consistent with the principles and novel features disclosed herein.

The invention claimed is:

1. A point of care apparatus comprising:

a fluid container configured to receive a biofluid, the fluid container having an open end, and wherein the open end of the fluid container includes an engageable portion;

an intermediate cap having a chamber formed between a first and second pierceable seal, the intermediate cap having an upwardly extending peripheral wall and a downwardly extending peripheral wall relative to the chamber, wherein the upwardly extending peripheral wall includes an engagement feature that couples the intermediate cap to the engageable portion of the fluid container;

a cartridge having at least one opening in a top surface that is in fluid communication with at least one microfluidic channel that extends within the cartridge, the cartridge having a collar that extends from the top surface and defines a passageway that is in fluid communication with the at least one opening in the cartridge, the collar having an engageable portion, wherein the downwardly extending peripheral wall of the intermediate cap includes an engagement feature that couples the cartridge with the engageable portion of the collar;

a first piercing insert configured between the first pierceable seal and the open end of the fluid container, the first piercing insert having a piercing feature and an opening extending through the first piercing insert, wherein engagement between the engagement feature of the upwardly extending peripheral wall of the intermediate cap and the engageable portion of the fluid container bias the piercing feature of the first piercing insert to pierce the first pierceable seal to place the fluid container in fluid communication with the chamber of the intermediate cap; and a second piercing insert configured between the second pierceable seal and the top surface of the cartridge, the second piercing insert having a piercing feature, wherein engagement between engagement feature of the downwardly extending peripheral wall of the intermediate cap and the engageable portion of the collar bias the piercing feature of the second piercing insert to pierce the second pierceable seal to place the at least one microfluidic channel in fluid communication with the chamber of the intermediate cap.

2. The point of care apparatus of claim 1, wherein the engageable portion of the open end of the fluid contain includes a threaded portion, wherein the engagement feature of the upwardly peripheral wall includes threads, wherein the threads are engageable with the threaded portion of the fluid container to reversibly couple the intermediate cap to the fluid container, wherein the engageable portion of the collar includes a threaded portion, and wherein engagement feature of the downwardly extending peripheral wall includes threads that are engageable with the threaded portion to reversibly couple the cartridge with the threaded portion of the collar.

3. The point of care apparatus of claim 1, wherein the chamber in the intermediate cap includes lysis reagents.

4. The point of care apparatus of claim 3, wherein the lysis reagents comprise proteinase K.

5. The point of care apparatus of claim 3, wherein the lysis reagents are in the form of lyophilized pellets.

6. The point of care apparatus of claim 1, wherein the second piercing insert is directly coupled to the top surface of the cartridge.

7. The point of care apparatus of claim 1 further comprising a spacer positioned in the collar, the spacer having at least one opening with a valve to reduce backflow of fluid to the at least one microfluidic channel.

8. The point of care apparatus of claim 1, wherein the chamber in the intermediate cap includes one or more reagents for performing an amplification reaction to generate amplification products of a target nucleic acid.

9. The point of care apparatus of claim 1, wherein the at least one microfluidic channel includes one or more reagents for performing an amplification reaction to generate amplification products of a target nucleic acid.

10. The point of care apparatus of claim 1 further comprising at least one heater, wherein the at least one heater is configured to heat the fluid container, the intermediate cap, the at least one microfluidic fluidic channel, or combinations thereof.

11. The point of care apparatus of claim 10, wherein the heater is configured to accelerate reaction kinetics of an amplification reaction of a target nucleic acid.

12. The point of care apparatus of claim 1, wherein the cartridge includes one or more vents in fluid communication with the at least one microfluidic channel, and wherein the one or more vents includes a gas permeable membrane.

13. The point of care apparatus of claim 1, wherein a closed end of the fluid container includes a diaphragm pump configured to dispense biofluids from the fluid container.

* * * * *